United States Patent
Tsai (10) Patent No.: US 10,147,503 B2
(45) Date of Patent: Dec. 4, 2018

(54) PERSONALIZE EXERCISE DECISION-MAKING DEVICE AND MANIPULATING METHOD FOR PATIENTS WITH CHRONIC DISEASES

(71) Applicant: National Yang-Ming University, Taipei (TW)

(72) Inventor: Jen-Chen Tsai, Taipei (TW)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 613 days.

(21) Appl. No.: 14/789,756

(22) Filed: Jul. 1, 2015

(65) Prior Publication Data

US 2016/0110513 A1  Apr. 21, 2016

Related U.S. Application Data

(60) Provisional application No. 62/064,730, filed on Oct. 16, 2014.

(51) Int. Cl.
G06F 9/44 (2018.01)
G06N 7/02 (2006.01)
G16H 50/20 (2018.01)
G06F 19/00 (2018.01)

(52) U.S. Cl.
CPC .......... *G16H 50/20* (2018.01); *G06F 19/00* (2013.01)

(58) Field of Classification Search
None
See application file for complete search history.

(56) References Cited

U.S. PATENT DOCUMENTS 5,706,822 A * 1/1998 Khavari ............... A63B 24/00
    482/9
2015/0012284 A1* 1/2015 Schenk ............... G06F 19/3481
    705/2

FOREIGN PATENT DOCUMENTS

EP     2541449     1/2013

OTHER PUBLICATIONS

American Diabetes Association "Physical Activity / Exercise and Diabetes Mellitus", Diabetes Care, 2003, pp. S73-S77.*

* cited by examiner

Primary Examiner — Li Wu Chang
(74) Attorney, Agent, or Firm — Muncy, Geissler, Olds & Lowe, PC (57) ABSTRACT

A personalize exercise decision-making device and manipulating method for patients with chronic diseases are disclosed from this invention. The device can provide an appropriate exercise suggestion to the user by the classification of the database based on the personal information, such as chronic diseases and drug administration, and the immediate physiological data. The device of the invention can also check the immediate physiological data, such as systolic blood pressure, diastolic blood pressure, heart rate and oxygenation concentration, to confirm the state of user whether can exercise. Further more, the device can monitor, analyze and store the physiological data for providing an instant feedback to user during the exercise. If the immediate physiological data of the user is over an exercise threshold in exercise, the device will provide a warning signal.

8 Claims, 10 Drawing Sheets

PERSONALIZE EXERCISE DECISION-MAKING DEVICE AND MANIPULATING METHOD FOR PATIENTS WITH CHRONIC DISEASES

CROSS-REFERENCE TO RELATED APPLICATIONS

This application claims priority of U.S. Provisional Application No. 62/064,730 filed on Oct. 16, 2014 under 35 U.S.C. § 119(e), the entire contents of which are hereby incorporated by reference.

FIELD OF THE INVENTION

The present invention relates to a personalize exercise decision-making device and manipulating method for patients with chronic diseases, and more particularly, to a personalize exercise decision-making device and manipulating method for patients with chronic diseases who taking medication. The chronic diseases may comprise diabetes mellitus and coronary artery disease, such as, but not limited to the listed ones.

BACKGROUND OF THE INVENTION

The health of chronic disease patients is needed to be controlled or managed through lifestyle (diet and exercise) and medications. The chronic disease include diabetes, heart disease, arthritis, kidney disease, HIV/AIDS, lupus, and multiple sclerosis. However, many patients suffer from more than one chronic disease (comorbidity). It is important to have an examination before starting an exercise action, and have an advice on what kind of exercises is safe. So the patients may prepare the precaution when doing exercise.

Exercise is a direct way to help chronic disease patient manage symptoms and improve health. Lack of exercise for patients with coronary artery disease may increase its risk of recurrence. For example, lack of exercise is a risk factor for developing coronary artery disease. Lack of physical activity can indirectly increase the risk of coronary artery disease, because it also increases the risk for diabetes and high blood pressure.

Currently, there is not a suitable wearable device may measure the physiological data, such as systolic blood pressure, diastolic blood pressure, heart rate and oxygenation concentration, to evaluate what types of exercise are best to chronic disease patients and how long of exercise can be done. For example, patient with overburdened heart may be carrying an extra pressure during exercise. On the other hand, although the physiological data of chronic disease patient is easy to be detected in the controlled environment, where the patient has to be sedated and supine, but it is still difficult to work in the ambulatory environment, where the activity of patient may affect sensors to produce error. Therefore, we should provide a personalize exercise decision to each patient with chronic diseases.

Comparing with the current case, the status of patient still need medical workers to analyze the physiological data detected from the wearable device. It can not provide quickly and accurately suggestion. In an embodiment, EP2541449 describes a physiological system which manages a diet and exercise plan for user, more particularly to a system capable of providing references for diet selection and recommendations for exercise to users based on the relations among diet, physical activity and personal physiological changes. However, the prior art does not evaluate the physiological condition and drug administration on influence of chronic disease patients during exercise. It is still failure to provide a personalize exercise suggestion.

Because of the wearable device in prior art is used for healthy people only, does not provide the personalize exercise suggestion based on physiological data, such as blood sugar, blood pressure, heart rate and oxygenation concentration, and drug administration for chronic disease patients. The present invention provides a solution to overcome the existing problems.

SUMMARY OF THE INVENTION

The present invention is a personalize exercise decision-making device to provide an appropriate exercise suggestion for the patients with chronic diseases, such as diabetes mellitus, coronary artery disease or hypertension, and the patients with comorbidity of coronary artery disease based on drug administration. The personalize exercise decision-making device not only improves convenience in using, but also helps to ensure the health of patients with chronic diseases in a best status.

In an embodiment of the invention, the personalize exercise decision-making device comprises a user interface having a data input region and a personalize exercise decision-making unit, wherein the data input region receiving a chronic medical record message and a drug administration from a user, and the personalize exercise decision-making unit displays an immediate physiological data and an appropriate exercise suggestion.

The personalize exercise decision-making device further comprises an exercise evaluation unit having a processing unit and a physiological detection unit electrically connected to the user interface, wherein the processing unit is further configured to determine a classification of sports based on the chronic medical record message and the drug administration, and the physiological detection unit detects the immediate physiological data, then sends the immediate physiological data to the personalize exercise decision-making unit.

The personalize exercise decision-making device further comprises an exercise decision unit having a physiological data management unit and an exercise data analysis processing unit electrically connected to the exercise evaluation unit and the user interface, wherein the physiological data management unit is further configured to store a physiological statistical data for chronic diseases corresponding to a plurality of classification of sports, the exercise data analysis processing unit is based on the immediate physiological data and the physiological statistical data for chronic diseases corresponding to the plurality of classification of sports to determine the appropriate exercise suggestion, then sends the appropriate exercise suggestion to the personalize exercise decision-making unit.

Another embodiment is a method implemented in a personalize exercise decision-making device for chronic patients to provide an appropriate exercise suggestion that comprises: providing the personalize exercise decision-making device to a user, inputting a chronic medical record message and a drug administration into a user interface of the personalize exercise decision-making device, wherein the personalize exercise decision-making device determines a classification of sports based on the chronic medical record message and the drug administration, detecting an immediate physiological data from the user, and the personalize exercise decision-making device provides the appropriate exercise suggestion based on the immediate physiological data and the physiological statistical data for chronic diseases corresponding to the plurality of classification of sports, and the user interface displays the immediate physiological data and the appropriate exercise suggestion.

Another embodiment is the drug administration comprises a confirmation on the user whether taking M1 medicine and M2 medicine.

Another embodiment is the chronic medical record message comprises a confirmation on the user age and the user whether has diabetes mellitus, coronary artery disease or hypertension.

Another embodiment is the plurality of classification of sports comprises a diabetes mellitus with coronary artery disease and taking M1 medicine, a diabetes mellitus with coronary artery disease and taking M2 medicine, and a diabetes mellitus without coronary artery disease or hypertension.

Another embodiment is the chronic medical record message further comprises a confirmation on the user whether has acute myocardial infarction or stable coronary artery disease, and a confirmation on the user whether has received coronary artery bypass grafting surgery or percutaneous coronary intervention when the user has coronary artery disease without diabetes mellitus and hypertension.

Another embodiment is the classification of sports further comprises a coronary artery disease with acute myocardial infarction, a coronary artery bypass grafting surgery, and a stable coronary artery disease or coronary artery disease with percutaneous coronary intervention.

Another embodiment is the immediate physiological data comprises one of a systolic blood pressure, a diastolic blood pressure, a heart rate and an oxygenation concentration.

Another embodiment is the physiological statistical data for chronic diseases is one of classification of sports comprising a limit of the systolic blood pressure, a limit of the diastolic blood pressure, a limit of the heart rate and a limit of the oxygenation concentration, then the appropriate exercise suggestion is a can not exercise suggestion when the immediate physiological data is not corresponding to the classification of sports limitation.

Another embodiment is the immediate physiological data corresponding to a physiological data of classification of sports and taking M1 medicine when the appropriate exercise suggestion is based on a scale for rating of perceived exertion and the exercise times spend.

Another embodiment is the appropriate exercise suggestion comprises an exercise goal heart rate and an exercise times spend when the immediate physiological data is corresponding to the classification of sports limitation and taking M2 medicine, or not taking M1 medicine and M2 medicine. The exercise goal heart rate is calculated based on the formula:

Exercise goal heart rate=[(220−Age)]−Resting heart rate]*Training intensity %+Resting heart rate Another embodiment is the device electrically connected to a storage medium for storing the immediate physiological data and the appropriate exercise suggestion.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION OF THE INVENTION

Having broadly summarized certain features of image conversion systems and methods of the present disclosure, reference will now be made in detail to the description of the disclosure as illustrated in the drawings. While the disclosure is described in connection with these drawings, there is no intent to limit the disclosure to the embodiment or embodiments disclosed herein. Although the description identifies or describes specifics of one or more embodiments, such specifics are not necessarily part of every embodiment, nor are all various stated advantages associated with a single embodiment. On the contrary, the intent is to cover all alternatives, modifications and equivalents included within the spirit and scope of the disclosure as defined by the appended claims. Further, it should be appreciated in the context of the present disclosure that the claims are not necessarily limited to the particular embodiments set out in the description.

The present invention provides a personalize exercise decision-making device for chronic diseases. The personalize exercise decision-making device can be worn on the user's arm, body or limbs. The best way to wear the personalize exercise decision-making device is on the user's arm showing as FIG. 1A. The components in FIGS. 1A and 1B disclose an embodiment to clearly illustrate the emphasis of the present invention. Moreover, in the drawings, similar reference numerals designate the corresponding parts throughout several views.

Figure 1A:
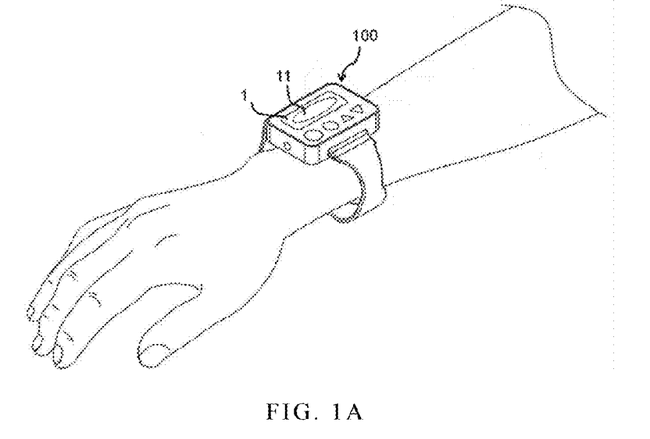
FIG. 1A reveals a wearing way of a personalize exercise decision-making device.
Figure 1B:
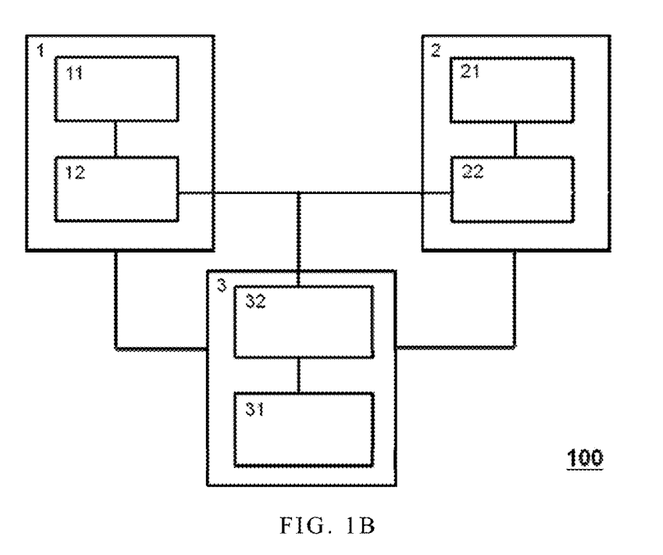
FIG. 1B reveals a system embodiment of the personalize exercise decision-making device.

Please refer to FIGS. 1A and 1B, which the personalize exercise decision-making device comprises a user interface 1, an exercise evaluation unit 2 and an exercise decision unit 3.

The user interface 1 is electrically connected with the exercise evaluation unit 2 and the exercise decision unit 3. The user interface 1 may be a touch panel. The user interface 1 comprises a data input region 11 to input a chronic medical record message of chronic diseases and drug administration, wherein the chronic medical record message comprises date, user name, sex, age and to confirm the user whether suffer from coronary artery disease, heart disease, diabetes mellitus or hypertension. The chronic medical record message further comprises to confirm the user whether suffer from more than one chronic disease (comorbidity). In some embodiments, the chronic medical record message comprises a confirmation on the user whether has acute myocardial infarction or stable coronary artery disease, and a confirmation on the user whether has received coronary artery bypasses grafting surgery or percutaneous coronary intervention when the user has coronary artery disease without diabetes mellitus and hypertension. The drug administration comprises a confirmation on the user whether taking M1 medicine or M2 medicine or not taking M1 medicine and M2 medicine. The M1 medicine may has an effect on exercise heart rate in a treatment, for example, comprises angiotensin converting enzyme inhibitor, β-blockers, Calcium Channel Blocker or Digitalis, etc. The M2 medicine does not have the effect on exercise heart rate in the treatment, for example, diuretic, anticoagulant, lipid-lowering drugs and antidiabetic drug, etc. The exercise decision unit 100 sends the immediate physiological data and the appropriate exercise suggestion to the personalize exercise decision-making unit 12, and the user interface 1 displays the immediate physiological data and the appropriate exercise suggestion.

The exercise evaluation unit 2 comprises a processing unit 21 and a physiological detection unit 22. The physiological detection unit 22 detects the immediate physiological data from the user. The immediate physiological data may include, but not limited, systolic blood pressure, diastolic blood pressure, heart rate and oxygenation concentration. Furthermore, the physiological detection unit 22 is electrically connected the user interface 1 to send the immediate physiological data to the personalize exercise decision-making unit 12, and the user interface 1 displays the immediate physiological data. The processing unit 21 determines a classification of sports based on the chronic medical record message and the drug administration.

The exercise decision unit 3 comprises a physiological data management unit 31 and an exercise data analysis processing unit 32, is electrically connected to the exercise evaluation unit 2 and the user interface 1. The physiological data management unit 31 is further configured to store a physiological statistical data for chronic diseases corresponding to a plurality of classification of sports. The physiological statistical data for chronic diseases corresponding to the plurality of classification of sports comprises diabetes mellitus with coronary artery disease or hypertension and taking M1 medicine, diabetes mellitus with coronary artery disease or hypertension and taking M2 medicine, and diabetes mellitus without coronary artery disease or hypertension. The sports further comprises a classification for patients with a coronary artery disease, an acute myocardial infarction, or has ever received a coronary artery bypass grafting surgery, and a classification for patients with a stable coronary artery disease, or has ever received percutaneous coronary intervention. The exercise data analysis processing unit 32 is based on the immediate physiological data and the physiological statistical data for chronic diseases corresponding to the plurality of classification of sports to determine the appropriate exercise suggestion. The appropriate exercise suggestion is sent to the user interface 1 by the exercise decision unit 3, and the personalize exercise decision-making unit 12 displays the appropriate exercise suggestion to user.

The personalize exercise decision-making device 100 except for providing the appropriate exercise suggestion through the user interface 1, the exercise evaluation unit 2 and the exercise decision unit 3 further monitors the immediate physiological data of the user in real time, and stores the immediate physiological data in a storage medium (not shown) during exercise or after exercise. The appropriate exercise suggestion is also stored in the storage medium. In particular, the immediate physiological data and the appropriate exercise suggestion are transferred to the cloud storage (not shown) over network. The personalize exercise decision-making device 100 determines a training program based on the immediate physiological data and the exercise record stored in the storage medium or the cloud storage. The personalize exercise decision-making device 100 provides the most easy way to proceed with the exercise training at home. Further, the medical workers provide an instant feedback to user based on the immediate physiological data and the exercise record stored in the cloud storage.

Figure 2:
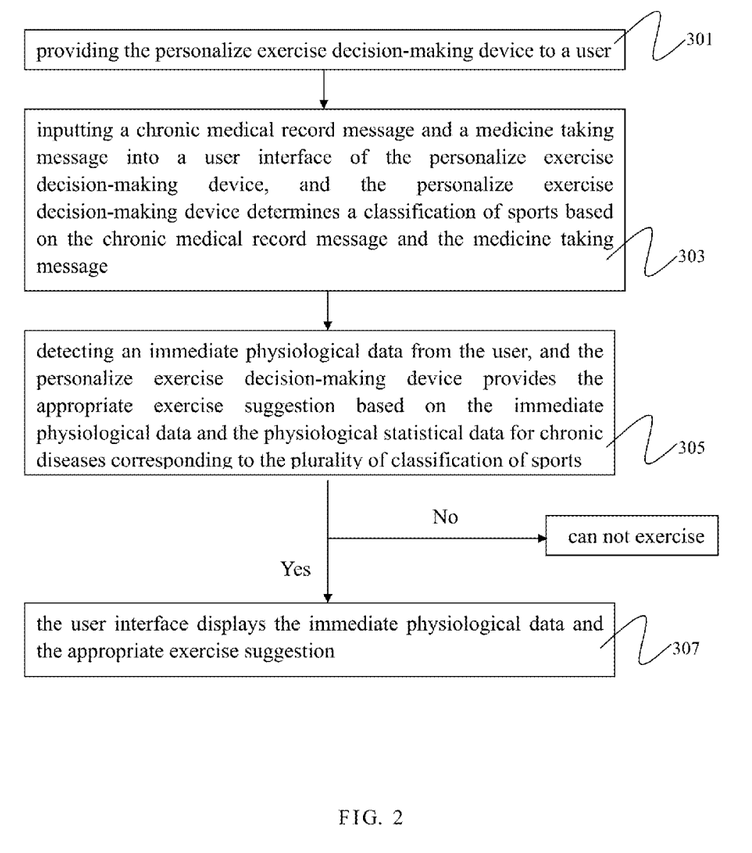
FIG. 2 reveals a flowchart to implement the personalize exercise decision-making device.
Figure 3:
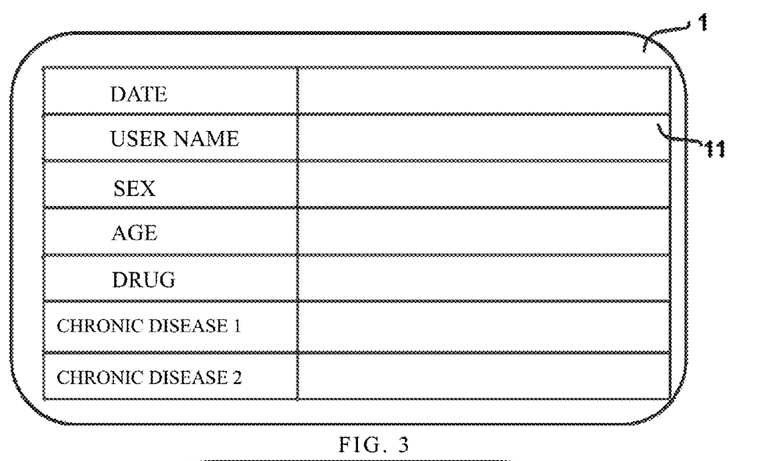
FIG. 3 reveals an user interface with a data input region.

Please refer to FIG. 2, which is a flowchart to implement the personalize exercise decision-making device. The flowchart of FIG. 2 may be viewed as an example of steps of a method implemented in the personalize exercise decision-making device 100 according to one or more embodiments. Beginning with block 310, the personalize exercise decision-making device 100 (FIGS. 1A and 1B) is provided to the user, such as patient with chronic conditions, to wear.

In block 303, inputting the chronic medical record message and a drug administration into the user interface 1 (FIGS. 1A and 1B) of the personalize exercise decision-making device 100 (FIGS. 1A and 1B). The personalize exercise decision-making device 100 (FIGS. 1A and 1B) determines a classification of sports based on the chronic medical record message and the drug administration of the user.

In block 305, the physiological detection unit 21 (FIG. 1B) automatically detects the immediate physiological data. The personalize exercise decision-making device 100 (FIGS. 1A and 1B) compares the immediate physiological data with the physiological statistical data for chronic diseases corresponding to the plurality of classification of sports to determine the user whether can exercise, and displays a message on the user interface 1 (FIGS. 1A and 1B).

In particular, the physiological statistical data may be one of classification of sports comprises a limit of the systolic blood pressure, a limit of the diastolic blood pressure, a limit of the heart rate and a limit of the oxygenation concentration, wherein the appropriate exercise suggestion provides a suggestion that can not exercise when the immediate physiological data is not corresponding to limit of classification of sports.

Figure 5A:
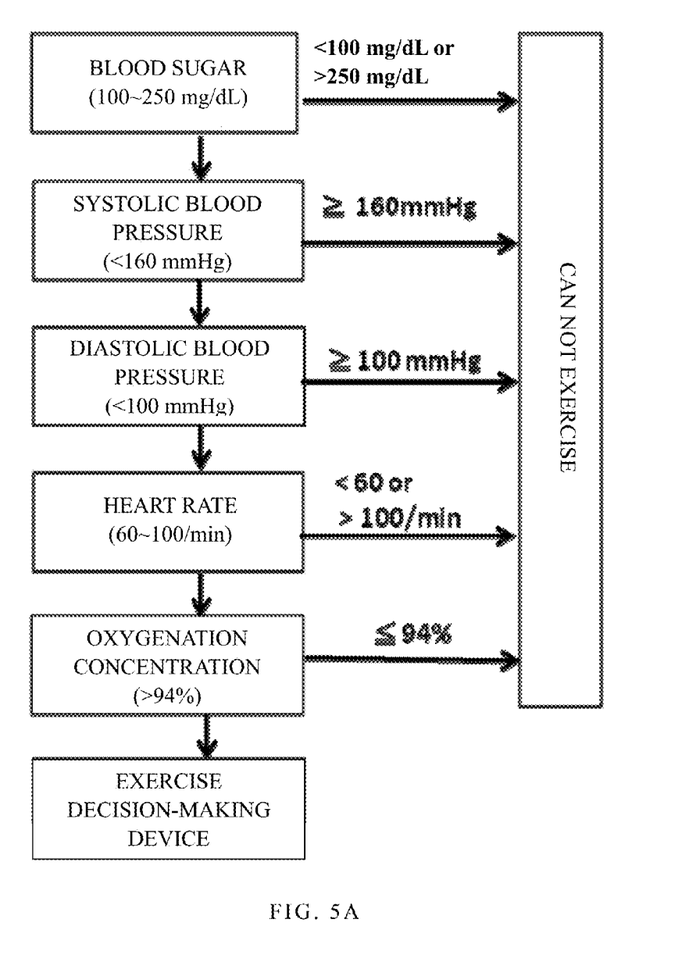
FIG. 5A reveals a flowchart to determine a patient with diabetes mellitus whether can exercise.

Please refer to FIG. 5A, FIG. 5A is a flowchart to determine a patient with diabetes mellitus whether can exercise. Please refer FIG. 5A, when the user with diabetes mellitus has a blood sugar (glucose) level higher than 250 mg/dL or less than 100 mg/dL, a systolic blood pressure is higher than 160 mmHg, a diastolic blood pressure higher or equal to 100 mmHg, a heart rate faster than 100 beats a minute or less than 60 beats a minute, and an oxygenation concentration less or equal to 94% then the patient with diabetes mellitus is not corresponding to limit of classification of sports. Therefore, the personalize exercise decision-making device 100 (FIGS. 1A and 1B) determines the user with diabetes mellitus can not exercise.

Figure 5B:
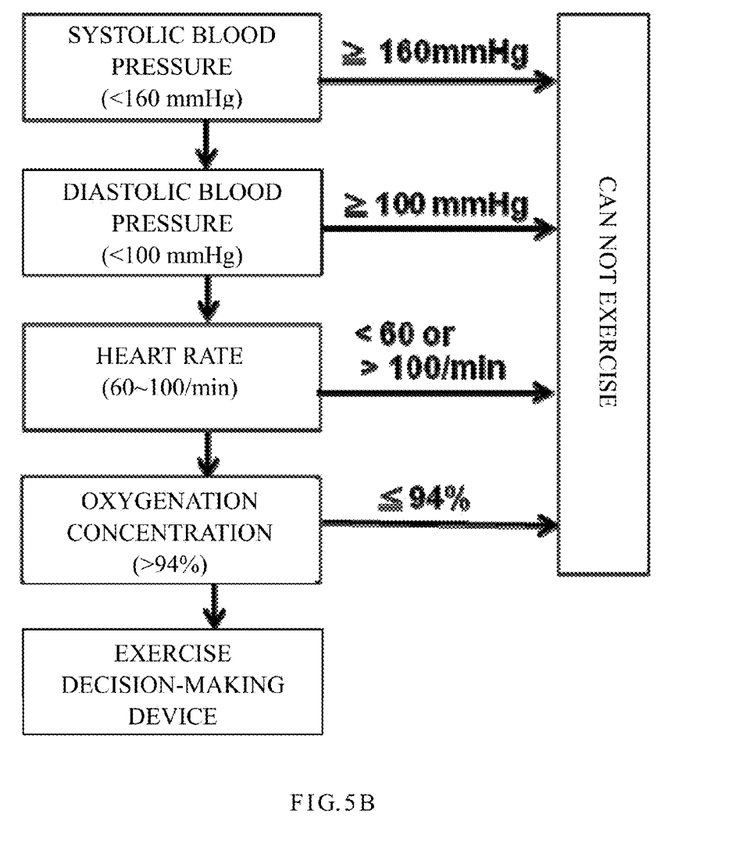
FIG. 5B reveals a flowchart to determine a patient with coronary artery disease whether can exercise.

Please refer to FIG. 5B, FIG. 5B reveals an flowchart to determine a patient with coronary artery disease whether can exercise. When the user with coronary artery disease has a systolic blood pressure higher than 160 mmHg, a diastolic blood pressure higher or equal to 100 mmHg, a heart rate faster than 100 beats a minute or less than 60 beats a minute, and an oxygenation concentration less or equal to 94% then the patient with coronary artery disease is not corresponding to the limit of sports classification. Therefore, the personalize exercise decision-making device 100 (FIGS. 1A and 1B) determines the user with coronary artery disease can not exercise.

In block 307, the appropriate exercise suggestion comprises an exercise goal heart rate and a exercise times spend when the immediate physiological data of the user corresponding to limit of classification of sports and the drug administration, for example, taking M2 medicine or a diabetes mellitus without coronary artery disease or hypertension, wherein the exercise goal heart rate is calculated based on the formula:

Exercise goal heart rate=[(220−Age)]−Resting heart rate]*Training intensity %+Resting heart rate The exercise intensity is also computed by the formula above.

Figure 4:
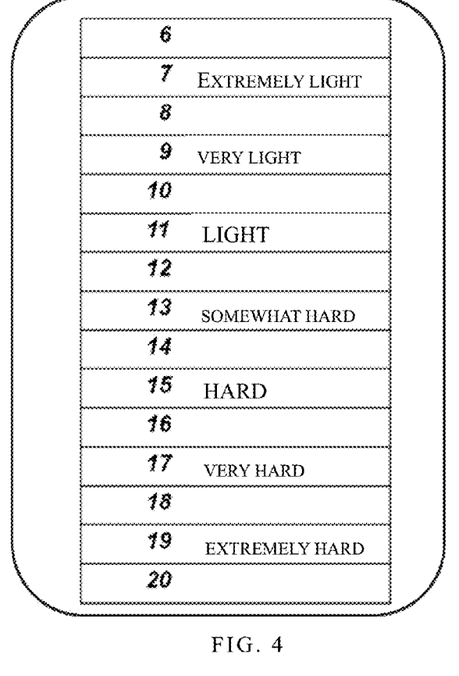
FIG. 4 reveals a scale for rating of perceived exertion.

In block 307, the appropriate exercise suggestion is based on a scale for rating of perceived exertion (RPE scale) and the exercise times spend when the immediate physiological data of the user is corresponding to limit of classification of sports and the drug administration, for example, taking M1 medicine. The scale for rating of perceived exertion is used to measure the intensity of exercise, and perceived exertion is how hard the personal body feels in working. It is based on the physical sensations of person experiences during exercise. FIG. 4 reveals a scale for rating of perceived exertion. The rating scale ranges from 6 to 20 in an activity, where the rating scale 6 means "no exertion at all", the rating scale 9 means "very light", the rating scale 11 means "light", the rating scale 13 means "somewhat hard", the rating scale 15 means "hard (heavy)", the rating scale 17 means "very hard", the rating scale 19 means "extremely hard", and the rating scale 20 means "maximal exertion."

Figure 6:
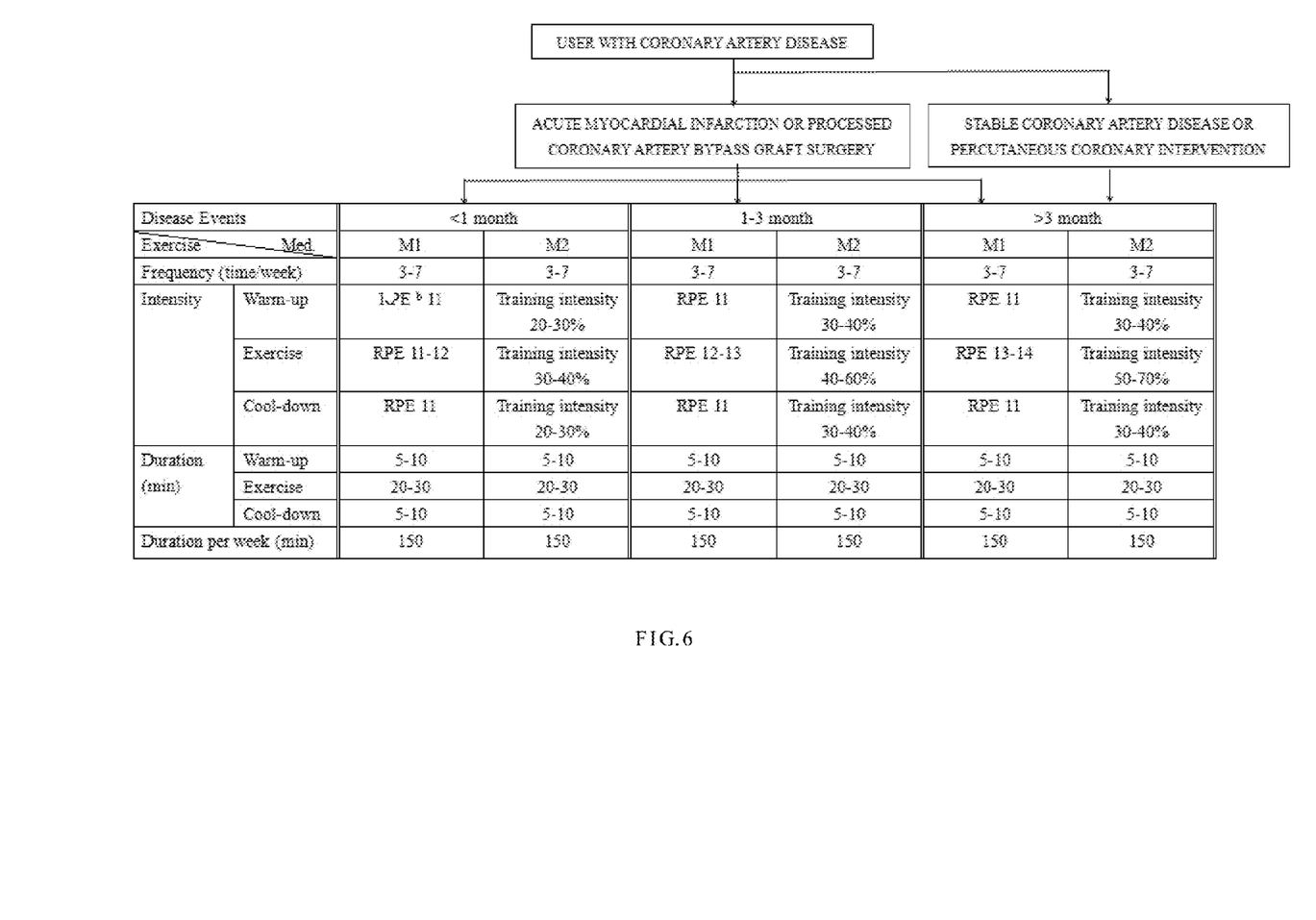
FIG. 6 reveals a flowchart to provide the appropriate exercise suggestion for coronary artery patients taking M1 medicine or M2 medicine.

Please refer to FIG. 6, FIG. 6 reveals a flowchart to provide the appropriate exercise suggestion for coronary artery patients taking M1 medicine or M2 medicine. The provided appropriate exercise suggestion is based on the scale for rating of perceived exertion and the exercise times spend when a user has contracted a disease or received a surgery for one month, wherein the user is a coronary artery patient with acute myocardial infarction, or have ever received a coronary artery bypass grafting surgery, and taking M1 medicine. The appropriate exercise suggestion is "warm-up" for 5 to 10 minutes based on the rating scale 11, the appropriate exercise suggestion is "exercise" for 20 to 30 minutes based on the rating scale 11 to 12, and the appropriate exercise suggestion is "cool-down" for 5 to 10 minutes based on the rating scale 11. However, the appropriate exercise suggestion may be different because of the user states change. When a user has contracted a disease or received a surgery for one month to three months, the rating scale of appropriate exercise suggestion "exercise" increases to 12 to 13. When a user has contracted a disease or received a surgery for up than three months, the rating scale of appropriate exercise suggestion "exercise" increases to 13 to 14.

As showing in FIG. 6, the appropriate exercise suggestion comprises an exercise goal heart rate and a exercise times spend when the patient with coronary artery disease has the drug administration, for example, taking M2 medicine, wherein the exercise goal heart rate is calculated based on the formula:

Exercise goal heart rate=[(220−Age)]−Resting heart rate]*Training intensity %+Resting heart rate The exercise intensity is also computed by the formula above.

The patient with coronary artery disease receives same suggestion for the exercise times spend when the patient takes M1 medicine or M2 medicine. However, the appropriate exercise suggestion is "warm-up" of training intensity 20~30% when a user has contracted acute myocardial infarction or received a surgical for one month, the appropriate exercise suggestion is "exercise" of training intensity 30~40%, the appropriate exercise suggestion is "cool-down" of training intensity 20~30%. Furthermore, the appropriate exercise suggestion is "warm-up" of training intensity 30~40% when a user has contracted acute myocardial infarction or received a surgical for one month to three months, the appropriate exercise suggestion is "exercise" of training intensity 40~60%, and the appropriate exercise suggestion is "cool-down" of training intensity 30~40%. When a user has contracted acute myocardial infarction or received a surgery for up than three months, the appropriate exercise suggestion is "exercise" of training intensity 50~70%.

Furthermore, in FIG. 6, if the user has stable coronary artery disease, coronary artery disease with percutaneous coronary intervention or has received a surgery for up than three months, and taking M1 or M2 medicine, the provided appropriate exercise suggestion is same as the user with acute myocardial infarction or receiving coronary artery bypass grafting surgery for up than three months, and taking M1 or M2 medicine.

The personalize exercise decision-making device 100 (FIGS. 1A and 1B) provides the appropriate exercise suggestion for the user with the comorbidity of coronary artery disease and taking M1 or M2 medicine. Shown in FIG. 6, the exercise frequency is 3~7 days a week, and the exercise duration is 150 minutes for a week.

Figure 7:
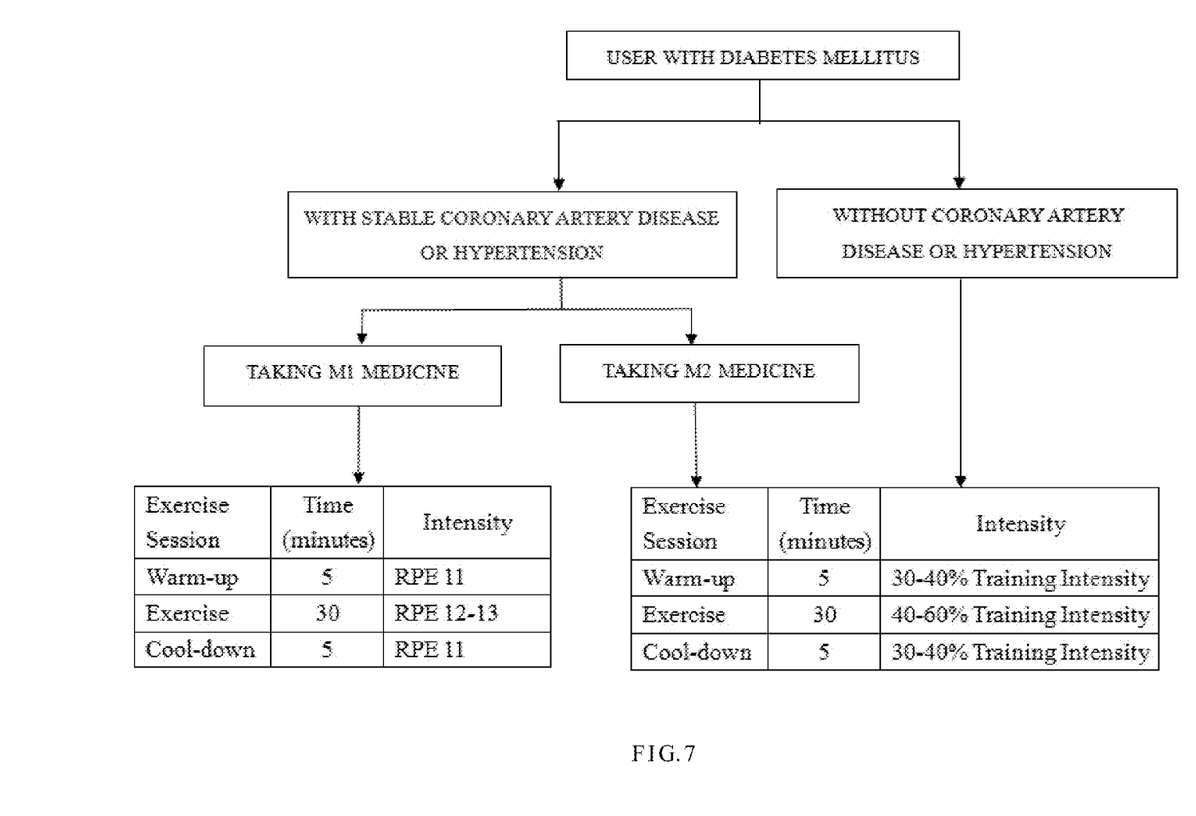
FIG. 7 reveals flowchart to provide the appropriate exercise suggestion for diabetes mellitus patients with or without coronary artery disease or hypertension, and taking M1 medicine or M2 medicine.

Please refer to FIG. 7, FIG. 7 reveals a flowchart to provide the appropriate exercise suggestion for diabetes mellitus patients with or without coronary artery disease or hypertension, and taking M1 medicine or M2 medicine. Shown in FIG. 7, the provided appropriate exercise suggestion is based on the exercise goal heart rate and the exercise times spend when the user has diabetes mellitus without coronary artery disease or hypertension. The appropriate exercise suggestion is "warm-up" for 5 minutes which exercise intensity is 30~40%, the appropriate exercise suggestion is "exercise" for 30 minutes which exercise intensity is 40~60%, and the appropriate exercise suggestion is "cool-down" for 5 minutes which exercise intensity is 30~40%, wherein the exercise goal heart rate is calculated based on the formula:

Exercise goal heart rate=[(220−Age)]−Resting heart rate]*Training intensity %+Resting heart rate When the user has diabetes mellitus with stable coronary artery disease or hypertension, and taking M2 medicine, the appropriate exercise suggestion is same as the user has diabetes mellitus without coronary artery disease or hypertension. However, the appropriate exercise suggestion is based on the scale for rating of perceived exertion and the exercise times spend when the user has diabetes mellitus with stable coronary artery disease or hypertension, and taking M1 medicine. The appropriate exercise suggestion is "warm-up" for 5 minutes based on the rating scale 11, the appropriate exercise suggestion is "exercise" for 30 minutes based on the rating scale 12 to 13, and the appropriate exercise suggestion is "cool-down" for 5 minutes based on the rating scale 11.

Figure 8A:
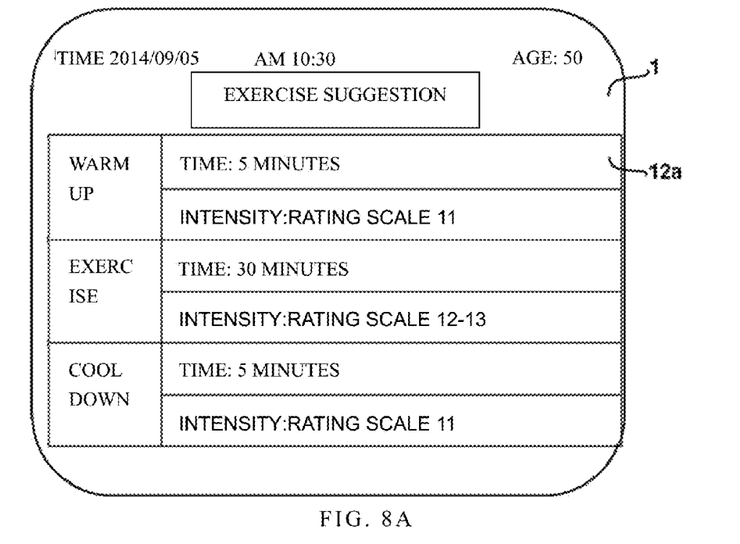
FIG. 8A reveals an appropriate exercise suggestion through the user interface for patients, age 50 years old, with diabetes mellitus, and taking M1 medicine.
Figure 8B:
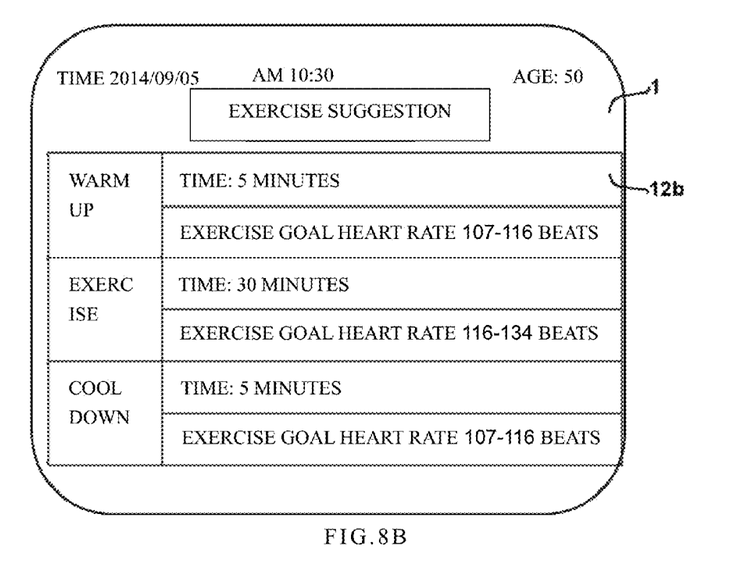
FIG. 8B reveals an appropriate exercise suggestion through the user interface for patients, age 50 years old, with diabetes mellitus, and taking M2 medicine.

In some embodiments, the appropriate exercise suggestion is based on the scale for rating of perceived exertion and the exercise times spend when the user has diabetes mellitus and taking M1 medicine. However, the appropriate exercise suggestion is based on exercise goal heart rate and the exercise times spend when the user has diabetes mellitus and taking M2 medicine. For example, two patients have diabetes mellitus, wherein the patient A is taking M1 medicine, and the patient B is taking M2 medicine; both patients are 50 years old with heart rate 80 beats a minute. Please refer to FIGS. 8A and 8B, the personalize exercise decision-making unit 12a provides the appropriate exercise suggestion is "warm-up" for 5 minutes based on the rating scale 11, the appropriate exercise suggestion is "exercise" for 30 minutes based on the rating scale 11 to 12, and the appropriate exercise suggestion is "cool-down" for 5 minutes based on the rating scale 11 when the patient A is 50 years old with diabetes mellitus and taking M1 medicine. The personalize exercise decision-making unit 12b provides the appropriate exercise suggestion is "warm-up" for 5 minutes which exercise goal heart rate from 107 to 116 beats a minute, the appropriate exercise suggestion is "exercise" for 30 minutes which exercise goal heart rate from 116 to 134 beats a minute, and the appropriate exercise suggestion is "cool-down" for 5 minutes which exercise goal heart rate from 107 to 116 beats a minute when the patient B is 50 years old with diabetes mellitus and taking M2 medicine.

Figure 9A:
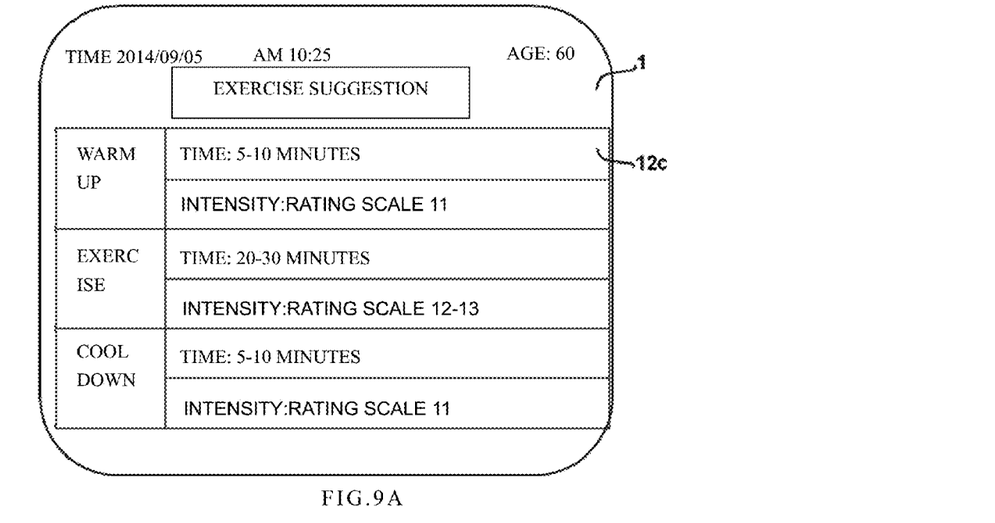
FIG. 9A reveals an appropriate exercise suggestion through the user interface for patients, age 60 years old, with acute myocardial infarction for two months, and taking M1 medicine.
Figure 9B:
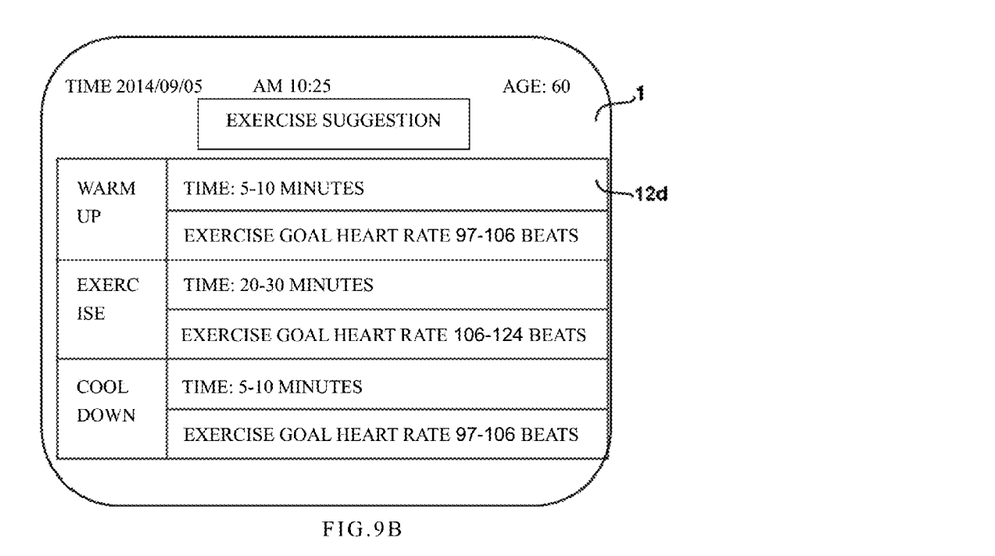
FIG. 9B reveals an appropriate exercise suggestion through the user interface for patients, age 60 years old, with acute myocardial infarction for two months, and taking M2 medicine.

In some embodiments, the appropriate exercise suggestion is based on the scale for rating of perceived exertion and the exercise times spend when the user has coronary artery disease (acute myocardial infarction or has received coronary artery bypass grafting surgery) and taking M1 medicine. However, the appropriate exercise suggestion is based on exercise goal heart rate and the exercise times spend when the user has coronary artery disease (acute myocardial infarction or has received coronary artery bypass grafting surgery) and taking M2 medicine. For example, two patients has acute myocardial infarction two months ago, wherein the patient C is taking M1 medicine, and the patient D is taking M2 medicine, both patients are 60 years old has heart rate 70 beats a minute. Please refer to FIGS. 9A and 9B, the personalize exercise decision-making unit 12c provides the appropriate exercise suggestion is "warm-up" for 5~10 minutes based on the rating scale 11. The appropriate exercise suggestion is "exercise" for 20~30 minutes based on the rating scale 11 to 12, and the appropriate exercise suggestion is "cool-down" for 5~10 minutes based on the rating scale 11 when the patient C is 60 years old with coronary artery disease and taking M1 medicine. The personalize exercise decision-making unit 12d provides the appropriate exercise suggestion is "warm-up" for 5~10 minutes which exercise goal heart rate from 97 to 106 beats a minute, the appropriate exercise suggestion is "exercise" for 20~30 minutes which exercise goal heart rate from 106 to 124 beats a minute, and the appropriate exercise suggestion is "cool-down" for 5~10 minutes which exercise goal heart rate from 97 to 106 beats a minute when the patient D is 60 years old with coronary artery disease and taking M2 medicine.

Figure 10A:
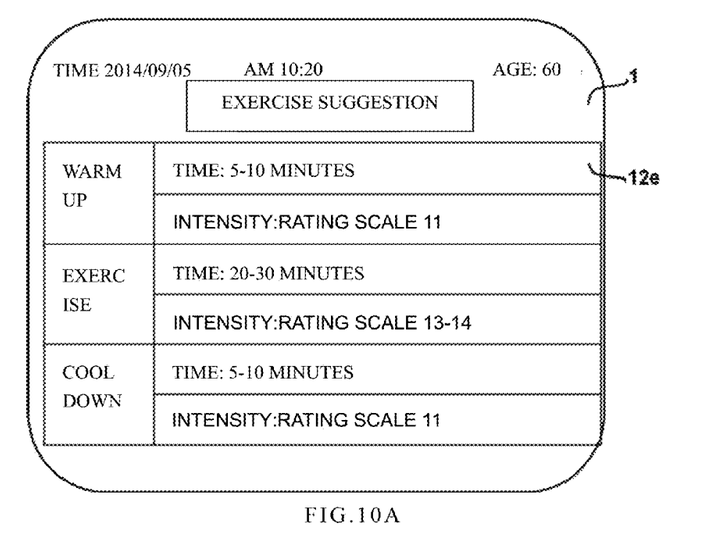
FIG. 10A reveals an appropriate exercise suggestion through the user interface for patients, age 60 years old, with stable coronary artery disease or has ever received percutaneous coronary intervention, and taking M1 medicine.
Figure 10B:
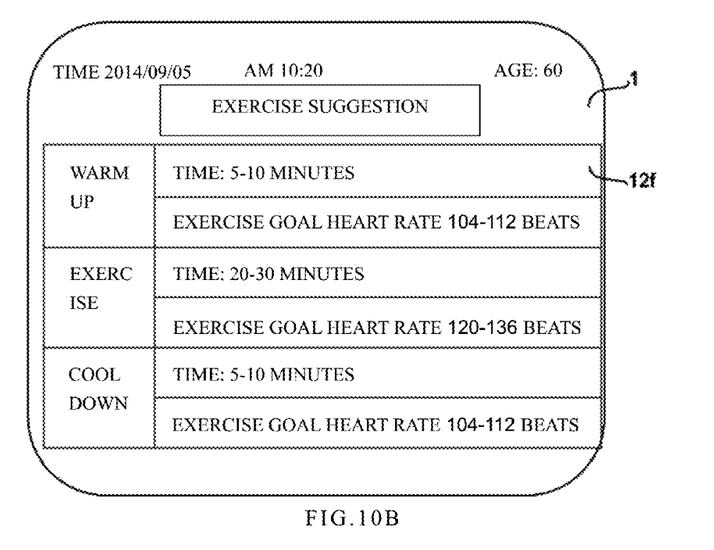
FIG. 10B reveals an appropriate exercise suggestion through the user interface for patients, age 60 years old, with stable coronary artery disease or has ever received percutaneous coronary intervention, and taking M2 medicine.

Please refer to FIG. 10A, the appropriate exercise suggestion is based on the scale for rating of perceived exertion and the exercise times spend when the user with stable coronary artery disease or coronary artery disease has received percutaneous coronary intervention, and taking M1 medicine. However, the appropriate exercise suggestion is based on exercise goal heart rate and the exercise times spend when the user with stable coronary artery disease or coronary artery disease has received percutaneous coronary intervention, and taking M2 medicine. For example, two patients both have stable coronary artery disease, wherein the patient E is taking M1 medicine and another patient F is taking M2 medicine; both patients are 60 years old with heart rate 80 beats a minute. FIGS. 10A and 10B reveals the appropriate exercise suggestion for the patient E and patient F. For the patient E is taking M1 medicine, the personalize exercise decision-making unit 12e provides the appropriate exercise suggestion is "warm-up" for 5~10 minutes based on the rating scale 11, the appropriate exercise suggestion is "exercise" for 20~30 minutes based on the rating scale 13 to 14, and the appropriate exercise suggestion is "cool-down" for 5~10 minutes based on the rating scale 11. For the patient F is taking M2 medicine, the personalize exercise decision-making unit 12f provides the appropriate exercise suggestion is "warm-up" for 5~10 minutes which exercise goal heart rate from 104 to 112 beats a minute, the appropriate exercise suggestion is "exercise" for 20~30 minutes which exercise goal heart rate from 120 to 136 beats a minute, and the appropriate exercise suggestion is "cool-down" for 5~10 minutes which exercise goal heart rate from 104 to 112 beats a minute.

The present invention provides a physiological warning unit is electrically connected to the physiological detection unit 22 (FIG. 1B). The physiological warning unit provides a warning signal when the immediate physiological data of the user is over an exercise threshold. The physiological warning unit provides the signal through the user interface 1 (FIGS. 1A and 1B). The personalize exercise decision-making device 100 (FIGS. 1A and 1B) may support any one type of warning signals, such as sound, light, video, image or any combination thereof. For an embodiment, the physiological warning unit provides the warning signal through the user interface 1 (FIGS. 1A and 1B) when the user with chronic conditions does not exercise in a period of time (e.g., 3 days) or spend time to exercise less than 150 minutes a week.

In view of the above description, the personalize exercise decision-making device 100 (FIGS. 1A and 1B) and manipulating method for patient with chronic diseases is described in block 303. The physiological detection unit 22 (FIG. 1B) determines the classification of sports based on the chronic medical record message and the drug administration (e.g., taking M1 medicine or M2 medicine) provided by the user interface 1 (FIGS. 1A and 1B) and processed by the processing unit 22 (FIG. 1B). The personalize exercise decision-making device 100 (FIGS. 1A and 1B) further measures the immediate physiological data and compares the immediate physiological data with the physiological statistical data for chronic diseases corresponding to the plurality of classification of sports to determine the user whether can exercise (block 305). The user interface 1 (FIGS. 1A and 1B) displays the immediate physiological data and the appropriate exercise suggestion when the personalize exercise decision-making device 100 (FIGS. 1A and 1B) analyzes and determines the user can exercise in real time (block 307). Moreover, the personalize exercise decision-making device 100 (FIGS. 1A and 1B) monitors the immediate physiological data of the user during exercise and analyzes the physiological statistical data for chronic diseases. The personalize exercise decision-making device 100 (FIGS. 1A and 1B) is able to interact with patients have chronic diseases through the user interface 1 (FIGS. 1A and 1B), and provide an instant feedback to patients to proceed with the exercise training at home. Specially, the personalize exercise decision-making device 100 (FIGS. 1A and 1B) is a multifunction body-building device with effective manipulating method for patients with chronic diseases to provide an evaluation before exercise, a personalize exercise making suggestion, a heart rate monitor during exercise and an instant feedback.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. A personalize exercise decision-making device for chronic patients, which is worn on a user's arm, comprising:
    a user interface, comprises:
        a data input region receives a chronic medical record message and a drug administration from the user, wherein the chronic medical record message comprises date, user name, sex, age, a confirmation on the user whether suffer from coronary artery disease, heart disease, diabetes mellitus or hypertension, a confirmation on the user whether suffer from more than one chronic disease and a confirmation on the user whether has received coronary artery bypasses grafting surgery or percutaneous coronary intervention when the user has coronary artery disease, wherein the drug administration comprises a confirmation on the user whether taking M1 medicine or M2 medicine; and
        a personalize exercise decision-making unit displays a real time physiological data and an appropriate exercise suggestion;
    an exercise evaluation unit electrically connects to the user interface, comprises:
        a processing unit determines a classification of sports by matching the chronic medical record message and the drug administration from the data input region with correspondent information of a plurality of classification of sports from a physiological data management unit; and
        a physiological detection unit, detects the real time physiological data from the user, then sends the real time physiological data to the personalize exercise decision-making unit and an exercise data analysis processing unit, wherein the real time physiological data comprises a real time blood sugar level value, a real time heart rate value, a real time blood pressure value and a real time oxygenation concentration value from the user, then the user interface displays the real time physiological data;
    an exercise decision unit electrically connects to the exercise evaluation unit and the user interface, comprises:
        the physiological data management unit stores a plurality of classification of sports, wherein the plurality of classification of sports are classified as a diabetes mellitus with stable coronary artery disease or hypertension and taking M1 medicine, a diabetes mellitus with stable coronary artery disease or hypertension and taking M2 medicine, a diabetes mellitus without coronary artery disease or hypertension, a coronary artery disease with acute myocardial infarction or a coronary artery bypass grafting surgery and taking M1 medicine, a coronary artery disease with acute myocardial infarction or a coronary artery bypass grafting surgery and taking M2 medicine, a stable coronary artery disease or coronary artery disease with percutaneous coronary intervention and taking M1 medicine, and a stable coronary artery disease or coronary artery disease with percutaneous coronary intervention and taking M2 medicine, wherein each of classification of sports comprises the appropriate exercise suggestion and a physiological statistical data wherein the physiological statistical data comprise a limit of the systolic blood pressure, a limit of the diastolic blood pressure, a limit of the heart rate, a limit of the blood sugar and a limit of the oxygenation concentration; and
        the exercise data analysis processing unit determines the appropriate exercise suggestion by corresponding the real time physiological data to the physiological statistical data belonging to the classification of sports from the processing unit, if any one of the real time physiological data is not corresponding to the physiological statistical data of the classification of sports, then the exercise data analysis processing unit sends a can not exercise suggestion, otherwise, the exercise data analysis processing unit sends the appropriate exercise suggestion to the personalize exercise decision-making unit.

2. The device of claim 1, wherein the appropriate exercise suggestion comprises an exercise goal heart rate and an exercise times spend when the real time physiological data is corresponding to the physiological statistical data belonging to the classification of sports from the processing unit and taking M2 medicine, wherein the exercise goal heart rate is calculated based on the formula:

$$\text{Exercise goal heart rate}=[(220-\text{Age})]-\text{Resting heart rate}]*\text{Training intensity \%}+\text{Resting heart rate}.$$

3. The device of claim 1, wherein the appropriate exercise suggestion is based on a scale for rating of perceived exertion and the exercise times spend when the real time physiological data is corresponding to the physiological statistical data belonging to the classification of sports from the processing unit and taking M1 medicine.

4. The device of claim 1, wherein the device is electrically connected a storage medium for storing the real time physiological data and the appropriate exercise suggestion.

5. A method implemented in a personalize exercise decision-making device for chronic patients to provide an appropriate exercise suggestion, comprising:
providing the personalize exercise decision-making device to a user, wherein the personalize exercise decision-making device is worn on the user's arm;
inputting a chronic medical record message into a user interface of the personalize exercise decision-making device, wherein the chronic medical record message comprises date, user name, sex, age, a confirmation on the user whether suffer from coronary artery disease, heart disease, diabetes mellitus or hypertension, a confirmation on the user whether suffer from more than one chronic disease and a confirmation on the user whether has received coronary artery bypasses grafting surgery or percutaneous coronary intervention when the user has coronary artery disease;
inputting a drug administration into the user interface of the personalize exercise decision-making device, wherein the drug administration comprises a confirmation on the user whether taking M1 medicine or M2 medicine;
the personalize exercise decision-making device determines a classification of sports from a plurality of classification of sports by matching the chronic medical record message and the drug administration with correspondent information of the plurality of classification of sports, wherein the plurality of classification of sports are classified as a diabetes mellitus with stable coronary artery disease or hypertension and taking M1 medicine, a diabetes mellitus with stable coronary artery disease or hypertension and taking M2 medicine, a diabetes mellitus without coronary artery disease or hypertension, a coronary artery disease with acute myocardial infarction or a coronary artery bypass grafting surgery and taking M1 medicine, a coronary artery disease with acute myocardial infarction or a coronary artery bypass grafting surgery and taking M2 medicine, a stable coronary artery disease or coronary artery disease with percutaneous coronary intervention and taking M1 medicine, and a stable coronary artery disease or coronary artery disease with percutaneous coronary intervention and taking M2 medicine;
wherein each of classification of sports comprises the appropriate exercise suggestion, wherein each of classification of sports comprises a physiological statistical data, wherein the physiological statistical data comprise a limit of the systolic blood pressure, a limit of the diastolic blood pressure, a limit of the heart rate, a limit of the blood sugar and a limit of the oxygenation concentration;
the personalize exercise decision-making device detects a real time physiological data from the user, wherein the real time physiological data comprises a real time blood sugar level value, a real time heart rate value, a real time blood pressure value and a real time oxygenation concentration value from the user, then the user interface displays the real time physiological data;
the personalize exercise decision-making device determines the appropriate exercise suggestion by corresponding the real time physiological data to the physiological statistical data belonging to the of classification of sports, if any one of the real time physiological data is not corresponding to the physiological statistical data of the classification of sports, then the appropriate exercise suggestion is a can not exercise suggestion, otherwise, the user interface displays the appropriate exercise suggestion from the classification of sports.

6. The method of claim 5, wherein the appropriate exercise suggestion comprises an exercise goal heart rate and an exercise times spend when the real time physiological data is corresponding to the physiological statistical data belonging to the classification of sports from the processing unit and taking M2 medicine, wherein the exercise goal heart rate is calculated based on the formula:

Exercise goal heart rate=[(220−Age)]−Resting heart rate]*Training intensity %+Resting heart rate.

7. The method of claim 5, wherein the real time physiological data is corresponding to the physiological statistical data belonging to the classification of sports from the processing unit and taking M1 medicine when the appropriate exercise suggestion is based on a scale for rating of perceived exertion and the exercise times spend.

8. The method of claim 5, wherein further comprising:
storing the real time physiological data and the appropriate exercise suggestion in a storage medium.

* * * * *